US010506433B2

(12) United States Patent
Mosenia et al.

(10) Patent No.: US 10,506,433 B2
(45) Date of Patent: Dec. 10, 2019

(54) SECURE OPTICAL COMMUNICATION CHANNEL FOR IMPLANTABLE MEDICAL DEVICES (71) Applicant: The Trustees of Princeton University, Princeton, NJ (US)

(72) Inventors: Arsalan Mosenia, Princeton, NJ (US); Niraj K. Jha, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 48 days.

(21) Appl. No.: 15/723,525

(22) Filed: Oct. 3, 2017

(65) Prior Publication Data
US 2018/0109946 A1 Apr. 19, 2018

Related U.S. Application Data (60) Provisional application No. 62/409,083, filed on Oct. 17, 2016.

(51) Int. Cl.
*A61N 1/00* (2006.01)
*H04W 12/06* (2009.01)
(Continued)

(52) U.S. Cl.
CPC .......... *H04W 12/06* (2013.01); *A61N 1/3727* (2013.01); *A61N 1/37217* (2013.01);
(Continued)

(58) Field of Classification Search
CPC ..... H04W 12/06; H04W 12/02; H04W 12/04; H04L 9/0861; H04L 2209/80;
(Continued)

(56) References Cited

U.S. PATENT DOCUMENTS

2014/0072119 A1* 3/2014 Hranilovic ............ H04L 9/3215
380/270
2016/0250490 A1* 9/2016 Hoffman ............ A61N 1/37252
607/60

OTHER PUBLICATIONS

A. M. Nia, M. Mozaffari-Kermani, S. Sur-Kolay, A. Raghunathan, and N. K. Jha, "Energy-efficient long-term continuous personal health monitoring," IEEE Trans. Multi-Scale Computing Systems, vol. 1, No. 2, pp. 85-98, 2015.
(Continued)

*Primary Examiner* — Scott M. Getzow
(74) *Attorney, Agent, or Firm* — Meagher Emanuel Laks Goldberg & Liao, LLP (57) ABSTRACT An implantable medical device (IMD) configured to communicate with an external device (ED). The ED supports two way RF communications and has a light source. The IMD includes a processor coupled to an optical detector, the processor is configured to verify that light is being received from the ED light source and that the ED is a trusted device, establishing a unidirectional optical channel from the ED to the IMD. An RF transceiver is coupled to the processor, the processor being configured permit two way RF communications with the ED only under a condition that the ED is verified as a trusted device. The processor may be configure to wake up periodically or aperiodically to check for the presence of light from the ED light source. The processor may be configured to detect a multi-bit message from the ED via the unidirectional optical channel. The multi-bit message may include a key.

18 Claims, 7 Drawing Sheets

(51) Int. Cl.
H04W 12/04 (2009.01)
H04W 12/02 (2009.01)
A61N 1/372 (2006.01)
H04L 9/08 (2006.01)
H04W 12/00 (2009.01)

(52) U.S. Cl.
CPC ..... *A61N 1/37223* (2013.01); *A61N 1/37254* (2017.08); *H04L 9/0861* (2013.01); *H04W 12/003* (2019.01); *H04W 12/02* (2013.01); *H04W 12/04* (2013.01); *H04L 2209/80* (2013.01); *H04L 2209/88* (2013.01)

(58) Field of Classification Search
CPC ............ H04L 2209/88; A61N 1/37254; A61N 1/37252; A61N 1/37217; A61N 1/37223; A61N 1/3727
See application file for complete search history.

(56) References Cited

OTHER PUBLICATIONS

D. Halperin, T. S. Heydt-Benjamin, B. Ransford, S. S. Clark, B. Defend, W. Morgan, K. Fu, T. Kohno, and W. H. Maisel, "Pacemakers and implantable cardiac defibrillators: Software radio attacks and zero-power defenses," in Proc. IEEE Symp. Security & Privacy, 2008, pp. 129-142.

S. Gollakota, H. Hassanieh, B. Ransford, D. Katabi, and K. Fu, "They can hear your heartbeats: Non-invasive security for implantable medical devices," ACM SIGCOMM Computer Communication Review, vol. 41, No. 4, pp. 2-13, 2011.

S. Lee, K. Fu, T. Kohno, B. Ransford, and W. H. Maisel, "Clinically significant magnetic interference of implanted cardiac devices by portable headphones," Heart Rhythm, vol. 6, No. 10, pp. 1432-1436, 2009.

C. Hu, F. Zhang, X. Cheng, X. Liao, and D. Chen, "Securing communications between external users and wireless body area networks," in Proc. ACM Wkshp. Hot Topics on Wireless Network Security and Privacy, 2013, pp. 31-36.

S. Schechter, "Security that is meant to be skin deep," Microsoft Research, Tech. Rep., Apr. 2010.

F. Xu, Z. Qin, C. C. Tan, B. Wang, and Q. Li, "IMDGuard: Securing implantable medical devices with the external wearable guardian," in Proc. IEEE Int. Conf. Computer Communications, 2011, pp. 1862-1870.

M. Rostami, A. Juels, and F. Koushanfar, "Heart-to-heart (H2H): Authentication for implanted medical devices," in Proc. ACM SIGSAC Conf. Computer & Communications Security, 2013, pp. 1099-1112.

T. Halevi and N. Saxena, "Acoustic eavesdropping attacks on constrained wireless device pairing," IEEE Trans. Information Forensics and Security, vol. 8, No. 3, pp. 563-577, 2013.

F.-M. Wu, C.-T. Lin, C.-C. Wei, C.-W. Chen, H.-T. Huang, and C.-H. Ho, "1.1-Gb/s white-LED-based visible light communication employing carrier-less amplitude and phase modulation," IEEE Photonics Technology Letters, vol. 24, No. 19, pp. 1730-1732, 2012.

A. Mosenia, S. Sur-Kolay, A. Raghunathan, and N. K. Jha, "CABA: Continuous authentication based on BioAura," under review, IEEE Trans. Computers, 2016.

"Is your defibrillator beeping?" https://keepyourhearthealthy.wordpress.com/2011/01/02/is-your-defibrillator-beeping/, accessed: Oct. 9, 2016.

"ATmega168," http://www.atmel.com/devices/atmega168.aspx, accessed: Oct. 9, 2016.

"Simblee," https://www.simblee.com/index.html, accessed: Oct. 9, 2016.

S. S. Clark and K. Fu, "Recent results in computer security for medical devices," in Proc. Int. Conf. Wireless Mobile Communication and Healthcare, 2011, pp. 111-118.

* cited by examiner

SECURE OPTICAL COMMUNICATION CHANNEL FOR IMPLANTABLE MEDICAL DEVICES

CROSS-REFERENCE TO PRIOR FILED APPLICATIONS

This application claims priority to U.S. provisional application 62/409,083 filed Oct. 17, 2016, which is incorporated herein in its entirety.

STATEMENT REGARDING FEDERALLY SPONSORED RESEARCH OR DEVELOPMENT

This invention was made with government support under Grants #CNS-1219570 and #CNS-1617628 awarded by the National Science Foundation. The government has certain rights in the invention.

FIELD OF THE INVENTION

The present disclosure generally relates to the field of implantable medical devices, and in particular systems and methods for establishing to secure communications with implantable medical devices using optical and RF communications channels.

BACKGROUND

Implantable medical devices (IMDs) are revolutionizing healthcare by offering continuous monitoring, diagnosis, and essential therapies for a variety of medical conditions. They can capture, process, and store various types of physiological signals, and are envisioned as the key to enabling a holistic approach to healthcare. Rapid technological advances in wireless communication, sensing, signal processing and low-power electronics are transforming the design and development of IMDs. State-of-the-art IMDs, e.g., pacemakers and implantable drug infusion systems, commonly support short-range wireless connectivity, which enables remote diagnosis and/or monitoring of chronic disorders and post-deployment therapy adjustment. Moreover, wireless connectivity allows healthcare professionals to non-intrusively monitor the device status, e.g., physicians can gauge the device battery level without performing any surgery.

Despite the numerous services that wireless connectivity offers, it may make an IMD susceptible to various security attacks. Previous research efforts have demonstrated how wireless connectivity may be a security loophole that can be exploited by an attacker. Improvements in this regard are needed.

SUMMARY OF THE INVENTION

An implantable medical device (IMD) is disclosed. The IMD is configured to communicate with an external device (ED). The ED is configured to support two way RF communications and has a light source. The IMD includes a processor coupled to an optical detector, the processor being configured to verify that light is being received from the ED light source and that the ED is a trusted device, establishing a unidirectional optical channel from the ED to the IMD. An RF transceiver is coupled to the processor, the processor being configured permit two way RF communications with the ED only under a condition that the ED is verified as a trusted device.

The processor may be configure to wake up periodically or aperiodically to check for the presence of light from the ED light source. The processor may be configure to determine an intensity of light received from the ED light source and determine if the intensity of the light received by the IMD is above a predetermined threshold. The processor may be configured to detect a multi-bit message from the ED via the unidirectional optical channel, the multi-bit message including a key.

The multi-bit message may include a pre sequence received prior to the key and a post sequence received after the key. The multi-bit message may include data or a command for the IMD. The ED may be configured to transmit the multi-bit message using a modulation scheme. The modulation scheme may include but is not limited to at least one of on-off keying (OOK), frequency-shift keying (FSK), amplitude-shift keying (ASK), amplitude and phase-shift keying (APSK), continuous phase modulation (CPM) and pulse-position modulation (PPM).

The processor may be configured to verify the multi-bit message from the ED to determine whether the ED is a trusted device. Following verification that the ED is a trusted device the processor may be configured to support encrypted communication via the RF transceiver using the key obtained via the unidirectional optical channel. The processor may be configured to generate a confirmation message encrypted using the key, the processor being configured to transmit the confirmation message to the ED via the RF transceiver. The ED may be configured determine whether the confirmation message can be successfully decoded using the key and only under this condition the ED is configured to support subsequent bi-directional RF communications with the IMD encrypted using the key A method of communicating using an implantable medical device (IMD) is also disclosed. The IMD is configured to communicate with an external device (ED). The ED is configured to support two way RF communications and has a light source. The method includes providing a processor coupled to an optical detector, the processor being configured to verify that light is being received from the ED light source and that the ED is a trusted device, establishing a unidirectional optical channel from the ED to the IMD. An RF transceiver is provided, the RF transceiver is coupled to the processor, the processor being configured permit two way RF communications with the ED only under a condition that the ED is verified as a trusted device.

The processor may be configure to wake up periodically or aperiodically to check for the presence of light from the ED light source. The processor may be configure to determine an intensity of light received from the ED light source and determine if the intensity of the light received by the IMD is above a predetermined threshold. The processor may be configured to detect a multi-bit message from the ED via the unidirectional optical channel, the multi-bit message including a key.

The multi-bit message may include a pre sequence received prior to the key and a post sequence received after the key. The multi-bit message may include data or a command for the IMD. The ED may be configured to transmit the multi-bit message using a modulation scheme. The modulation scheme may include but is not limited to at least one of on-off keying (OOK), frequency-shift keying (FSK), amplitude-shift keying (ASK), amplitude and phase-shift keying (APSK), continuous phase modulation (CPM) and pulse-position modulation (PPM).

The processor may be configured to verify the multi-bit message from the ED to determine whether the ED is a trusted device. Following verification that the ED is a trusted device the processor may be configured to support encrypted communication via the RF transceiver using the key obtained via the unidirectional optical channel. The processor may be configured to generate a confirmation message encrypted using the key, the processor being configured to transmit the confirmation message to the ED via the RF transceiver. The ED may be configured determine whether the confirmation message can be successfully decoded using the key and only under this condition the ED is configured to support subsequent bi-directional RF communications with the IMD encrypted using the key.

DETAILED DESCRIPTION

Despite the numerous services that wireless connectivity offers, it may make an IMD susceptible to various security attacks. Previous research efforts have demonstrated how wireless connectivity may be a security loophole that can be exploited by an attacker. For example, Halperin et al. "*Pacemakers and implantable cardiac defibrillators: Software radio attacks and zero-power defenses*" Proc. IEEE Symp. Security & Privacy, 2008, pp. 129-142 shows how an attacker can exploit the security susceptibilities of the wireless protocol utilized in an implantable cardioverter defibrillator (ICD) to perform a battery-draining attack against the device. This is an attack that aims to deplete the device battery by frequently activating/using the RF module. Moreover, they show that it is feasible to exploit these susceptibilities to change on-device data or the current operation of the device. Gollakota et al. "*They can hear your heartbeats: Non-invasive security for implantable medical devices*" ACM SIGCOMM Computer Communication Review, vol. 41, no. 4, pp. 2-13, 2011 explains how an adversary can eavesdrop on an insecure (i.e., unencrypted) communication channel between an IMD and its associated external device to extract sensitive information about the patient, e.g., the patient's electrocardiogram (ECG) readings.

To prevent battery-draining attacks, an attack-resilient wakeup protocol, which activates the RF module before every authorized communication, must be used. Today's IMDs often employ a magnetic switch, which turns on their RF module in the presence of an external magnet. Unfortunately, it has been shown that magnetic switches cannot prevent battery-draining attacks since they can be easily activated by an attacker (without the presence of a nearby magnet) if a magnetic field of sufficient strength is applied.

In order to secure the RF wireless channel between the IMD and the external device and avert the risk of eavesdropping on the channel, the use of cryptographic techniques, e.g., data encryption, has been suggested. However, traditional cryptographic techniques are not suitable for IMDs due to limited on-device resources, e.g., limited storage and battery energy. For example, asymmetric encryption mechanisms are not applicable to resource-constrained IMDs since they would significantly decrease the IMD battery lifetime. Several lightweight symmetric encryption mechanisms have been proposed in the last decade to ensure the security of communication protocols utilized in IMDs. See e.g., C. Strydis et al., "*Profiling of symmetric encryption algorithms for a novel biomedical-implant architecture*" in Proc. ACM Conf. Computing Frontiers, 2008, pp. 231-240 for a survey. While symmetric cryptography may offer a secure lightweight solution, it is greatly dependent on a secure key exchange protocol. Such a protocol enables sharing of the encryption key between the IMD and the external device. As extensively herein, previously-proposed key exchange protocols have various shortcomings since they either add significant overheads to the IMD or are susceptible to remote eavesdropping.

This disclosure includes practical key exchange and wakeup protocols, which complement lightweight symmetric encryption mechanisms, to thwart common security attacks against insecure communication channels. This disclosure also includes a secure optical communication channel (OpSecure). This disclosure contains the design and implementation of a low-power wakeup protocol and a secure key exchange protocol based on OpSecure. Several important aspects include:

1. OpSecure, an optical secure unidirectional (from the external device to the IMD) communication channel.

2. An attack-resilient low-power wakeup protocol for IMDs based on Op Secure.

3. A secure key exchange protocol, which enables sharing of the encryption key between IMDs and their associated external devices.

4. The design and implementation of a prototype IMD platform that supports the proposed protocols and present evaluation results for the prototype.

Disclosed below is a detailed description of the system and an explanation as to why wakeup and key exchange protocols are essential for IMDs along with a discussion of the shortcomings of previously-proposed protocols. The OpSecure system is presented in detail. Also disclosed is a wakeup protocol and a key exchange protocol based on OpSecure and a prototype and experimental setup. The prototype implementation is evaluated in connection with both protocols (wakeup and key exchange).

Wakeup and Key Exchange Protocols

Figure 1:
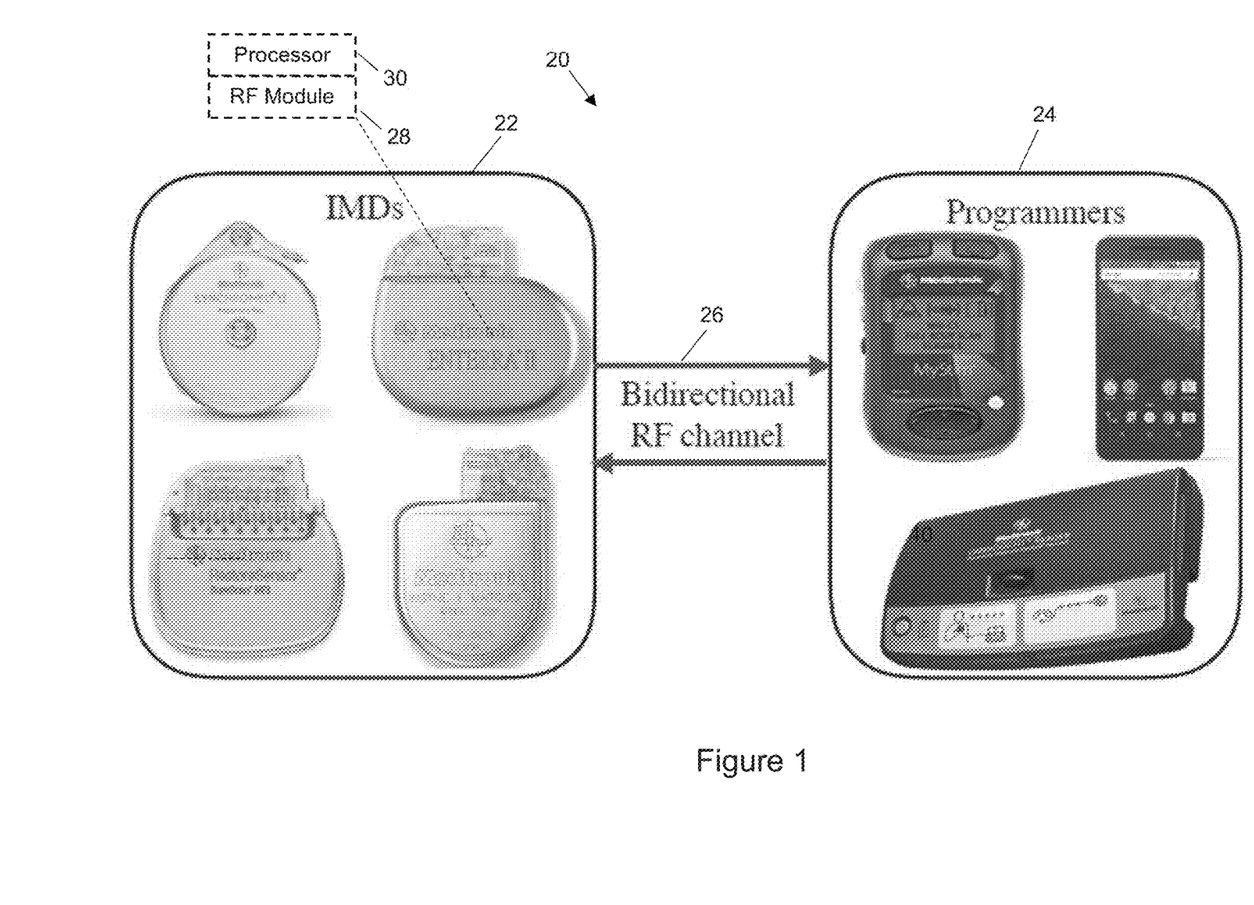
FIG. 1 is a basic IMD system architecture including an IMD and external device have a bidirectional RF channel that supports symmetric encryption.

As mentioned earlier, the IMD and its associated external device commonly have an RF channel that is used for bidirectional data communication. FIG. 1 is a basic system architecture 20 including an IMD (several examples shown generally by reference number 22) and external device (several examples shown generally by reference number 24) having a bidirectional RF channel 26 that supports symmetric encryption, e.g., Bluetooth (low energy). It is assumed that both devices are capable of using symmetric encryption for protecting the data sent over the RF channel.

The IMD includes an RF module shown generally by reference number 28 and at least one processor shown generally by reference number 30. Due to severe on-sensor energy constraints, the RF module 28 must be enabled only when absolutely needed, e.g., when an authorized physician wants to access on-device data. Thus, prior to each data transmission, the RF module 28 should be activated using a pre-defined wakeup protocol. This protocol must satisfy two main design requirements. First, it must be resilient against battery-draining attacks so that an attacker cannot activate the RF module. Second, it should add negligible size and energy overheads to the device.

After enabling the RF module 28 by the wakeup protocol, data can be transmitted over the bidirectional communication channel 26 with symmetric encryption. Since symmetric encryption is based on an encryption key, an exchange protocol must be used to securely exchange the encryption key between the IMD and the external device. A practical key exchange protocol must satisfy the following design requirements. First, it must guarantee the confidentiality of the encryption key and be resilient to remote eavesdropping. Second, its size and energy overheads must be minimal. Third, it must ensure that healthcare professionals can access and control the IMD without a notable delay in an emergency situation in which the patient needs immediate medical assistance.

Wakeup Protocols

As mentioned earlier, a magnetic switch is commonly integrated into today's IMDs to turn on the RF module when needed. However, magnetic switches are vulnerable to battery-draining attacks since they can be remotely activated. A few wakeup protocols have recently been presented in the academic literature. For example, the wakeup protocol presented by Halperin et al. "*Pacemakers and implantable cardiac defibrillators: Software radio attacks and zero-power defenses*" in Proc. IEEE Symp. Security & Privacy, 2008, pp. 129-142 relies on an authentication technique in which the IMD harvests the RF energy supplied by the external device itself. The RF module is powered by the battery only after the external device is authenticated. However, the RF energy harvesting subsystem needs an antenna, which imposes a significant size overhead on the IMD. Kim et al. "*Vibration-based secure side channel for medical devices*" in Proc. IEEE Design Automation Conference, 2015, pp. 1-6 suggest a wakeup scheme in which the IMD activates the RF module when it detects the vibration generated by an external electrical motor. Their scheme adds minimal size and energy overheads to the IMD since it only needs the addition of a low-power accelerometer to the IMD. However, in practice, the patient's regular activities, e.g., running, may unintentionally and frequently turn on the RF module, and as a result, deplete the device battery.

Key Exchange Protocols

The use of a pre-defined password, which is stored on the device and known to the user, is a longstanding tradition in the security community. However, a key exchange approach that needs active user involvement, e.g., asking the user to remember a password and give it to authorized physicians upon request, is not suitable for IMDs since the user may not be able to cooperate with healthcare professionals in an emergency, e.g., when the patient is unconscious. In order to minimize user involvement, previous research studies have proposed several user-independent key exchange protocols. These approaches and their shortcomings are discussed below.

Ultraviolet tattoos: Schechter, "*Security that is meant to be skin deep*" Microsoft Research, Tech. Rep., April 2010 presented a scheme in which a fixed user-selected human-readable key is tattooed directly on the patient's body using ultraviolet ink. In this protocol, all devices that need to communicate with the IMD must be equipped with a small, reliable, and inexpensive ultraviolet light-emitting diode and an input mechanism for key entry. This tattoo-based approach has two limitations. First, the design requires the patient to agree to acquire a tattoo, which significantly limits its applicability. Second, if the password becomes compromised, access by the attacker cannot be prevented easily since the password cannot be changed in a user-convenient manner.

Physiological signal-based key generation: A few physiological signal-based key generation protocols have been proposed. These can be used to generate a shared key for the IMD and the external device from synchronized readings of physiological, such as ECG, signals. Unfortunately, the robustness and security properties of keys generated using such techniques have not been well-established.

Using acoustic side channel: Halperin et al. "*Pacemakers and implantable cardiac defibrillators: Software radio attacks and zero-power defenses*" in Proc. IEEE Symp. Security & Privacy, 2008, pp. 129-142 presented a key exchange protocol based on acoustic side channels. Unfortunately, their protocol is susceptible to remote acoustic eavesdropping attacks and, as a result, does not offer a secure key exchange protocol. Moreover, it is not reliable in noisy environments since they utilized a carrier frequency within the audible range. Furthermore, it imposes a significant size overhead.

Using vibration side channel: Kim et al. "*Vibration-based secure side channel for medical devices*" in Proc. IEEE Design Automation Conference, 2015, pp. 1-6 proposed a key exchange protocol that relies on a vibration side channel, i.e., a channel in which the transmitter is a vibration motor, and the receiver is an accelerometer embedded in the IMD. This protocol requires negligible size and energy overheads. However, it has two shortcomings. First, since electrical motors generate capturable electromagnetic and acoustic waves during their normal operation, an adversary might be able to extract the key from signals leaked from the vibration motor. Second, since the method uses an accelerometer to detect vibrations, regular physical activities, e.g., running, may be interpreted as key transmission. This can reduce the battery lifetime of the IMD since the device needs to listen to the communication channel even when there is no actual transmission.

The system disclosed herein addresses the above-mentioned shortcomings of previously-proposed protocols, in particular size/energy overheads and vulnerability to eavesdropping, through a simple low-power, yet secure, key exchange protocol using visible light.

OpSecure: Secure Unidirectional Optical Data Transmission Channel

Optical data transmission (also called light-based wireless communication) is a well-known communication type that has attracted increasing attention in recent years due to its potential to offer high-speed wireless communication (as a complement or an alternative to WiFi) for a variety of portable devices, e.g., smartphones and laptops. Previous research studies demonstrate that optical communication channels can enable high-rate data transmission (the transmission rate can vary from several hundred Mb/s to a few Gb/s). In an optical channel, data packets flow from a light source (transmitter) to a light sensor (receiver). In order to establish a bidirectional communication channel between two devices, both devices must include an optical transceiver i.e., both devices must have a light source and a light sensor or detector.

There is a basic domain-specific challenge that must be addressed when developing an optical communication scheme for IMDs: integration of light sources into IMDs imposes significant size and energy overheads on these resource-constrained devices. It is not feasible to transmit data from an IMD to an external device via an optical channel even though such a channel can potentially enable two-way communication. Unlike light sources, state-of-the-art already-in-market light sensors are sufficiently compact and energy-efficient to be embedded in IMDs. Therefore, a unidirectional (one-way) communication channel, which transmits data from the external device to the IMD, can be implemented with minimal size and energy overheads. OpSecure is a secure unidirectional optical data communications channel implemented in this fashion.

OpSecure is intrinsically secure due to its close proximity requirement and high user perceptibility. Visible light attenuates very quickly as it passes through tissues in the body and, hence, can only be captured within a very close range. As demonstrated below, if the light source is in contact with the body and directed at the IMD, it can penetrate deep enough into the body to reach the IMD. However, a passive adversary cannot eavesdrop on OpSecure without an eavesdropping device attached to the body, which is very likely to be noticed by the patient.

Figure 2:
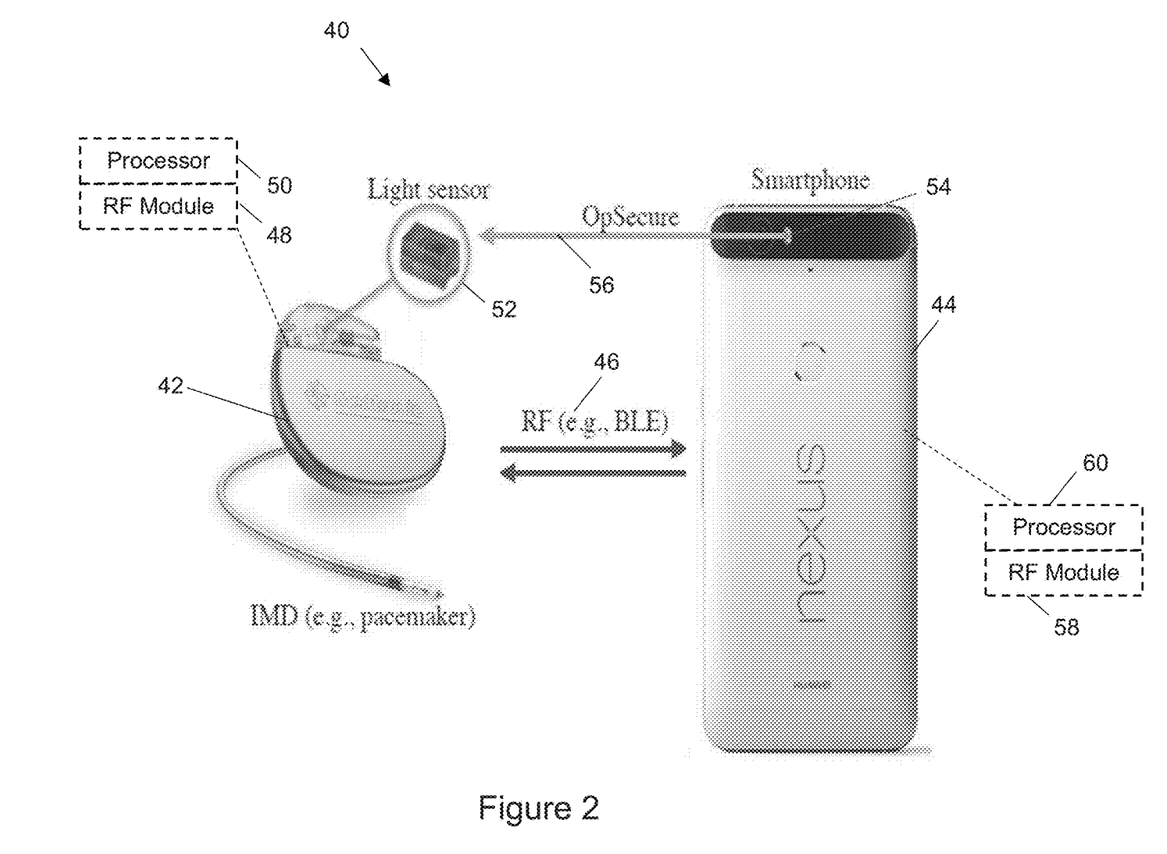
FIG. 2 is a diagram of an IMD system including an IMD (pacemaker) with an embedded light sensor and an external device (smartphone) with a flashlight that acts as a light source.

As illustrated in FIG. 1, the external device 24 may vary from specialized IMD programmers, i.e., external devices that are specifically designed to query the IMD data or send commands to the IMD, to general-purpose portable devices, e.g., smartphones. FIG. 2 is a diagram of a prototype IMD system including an IMD 42 (pacemaker) with an embedded light sensor 52 and an external device 44 (smartphone) with a LED 54 (flashlight) that acts as a light source 54. The IMD 42 includes an RF module 48 that is configured to couple to an RF module 58 in the smartphone. It should also be understood that the smartphone includes a processor 60 configured with an operating system and application software that can operate the LED 54 and the RF module 58. In general, the LED 54 and the light sensor 54 are configured to establish a unidirectional optical communication channel from the external device 44 to the IMD 42 as shown generally by arrow 56 (OpSecure).

This configuration has several advantages including but not limited to the following. First, the component needed in the external device for establishing the optical communication channel 56 are already present in smartphones (the LED 54 is used as a light source). Second, smartphones have become the dominant form of base stations for a large number of medical devices since they are ubiquitous and powerful, and incorporate various technologies needed for numerous applications. As a result, they can be used as a base station for collecting and processing several types of physiological data (including data collected by IMDs). Third, smartphones can easily support highly-secure encrypted transmission, which deters several potential attacks against the IMD. However, OpSecure can also be implemented on other devices that are used to communicate with the IMD, at minimal overheads, if they can be equipped with a small light source and an input mechanism for key entry.

Wakeup Protocol

Figure 3:
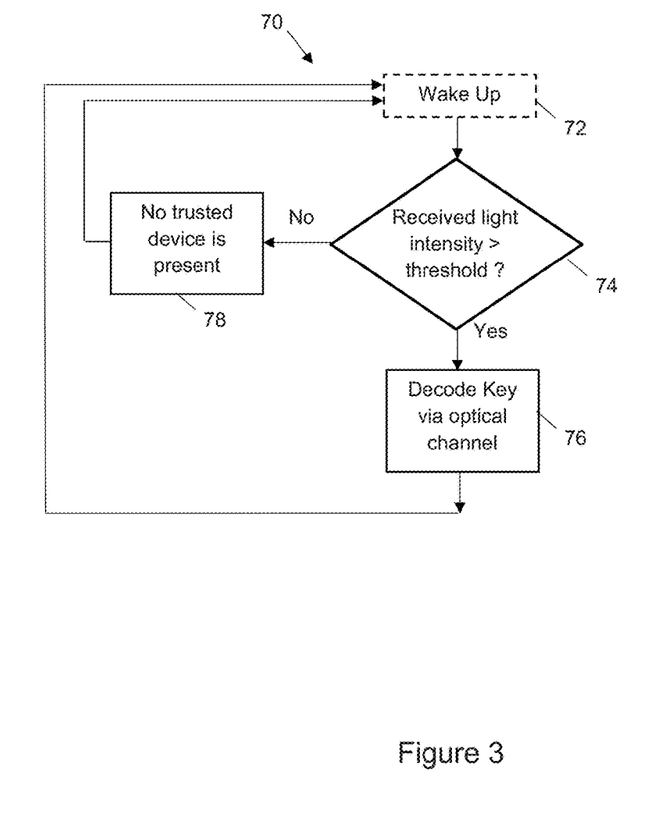
FIG. 3 is a basic flow chart showing the detection of a trusted device.

FIG. 3 is a basic flow chart showing the detection of a trusted device. It should be understood that any flowcharts contained herein are illustrative only and that other program entry and exit points, time out functions, error checking routines and the like (not shown) would normally be implemented in typical system software. It is also understood that system software may run continuously after being launched. Accordingly, any beginning and ending points are intended to indicate logical beginning and ending points of a portion of code that can be integrated with other portions of code and executed as needed. The order of execution of any of the blocks may also be varied without departing from the scope of this disclosure. Implementation of these aspects is readily apparent and well within the grasp of those skilled in the art based on the disclosure herein.

As mentioned earlier, when the light source is in contact with the human body, visible light can penetrate deep enough into the body to reach the IMD. However, it attenuates very quickly as it passes through the skin and/or other tissues in the body. We exploit this fundamental characteristic of visible light to develop a wakeup protocol that works as follows. The smartphone fully turns on its flashlight and the IMD wakes up periodically (or aperiodically) as shown by block 72. The IMD then check if a light source is present on the exterior of the body, i.e., it checks if the intensity of the light received by the IMD is above a pre-defined threshold as generally shown by block 74. If no light source is present, control is passed to block 78 and no trusted device is present. The IMD then waits for the next wakeup as shown by block 72. The presence of an on-body light source that points to the IMD is interpreted as the presence of a trusted external device as and control is passed to block 78. So long as a trusted device is present the IMD will decode an encryption key via the unidirectional optical channel. This key will be used subsequently for encryption of RF communications.

As discussed below, the wakeup protocol adds minimal size and energy overheads to the device. Unlike a majority of previously-proposed protocols, it also provides immunity against battery-draining attacks. In fact, an attacker, who wants to wake up the RF module, needs to attach a light source to the patient's body at a location close to the IMD. Such an action can be easily detected by the patient.

RF Key Exchange Protocol

Assuming the IMD and the external device use a bidirectional RF communication protocol that supports symmetric encryption, the protocol disclosed below can be used to transmit a randomly-generated key from the smartphone to the IMD. For each key exchange:

Step 1:

The smartphone first generates a random key $K \in \{0,1\}$ $N=k_1k_2 \ldots k_N$ of length N, and prepares a key packet as $Key_{packet}=Pre\|K\|Post$, where Pre and Post are two fixed binary sequences that are concatenated with the key to mark the beginning and end of a key packet.

Step 2:

The physician places the smartphone on the patient's body so that its flashlight is directed at the light sensor of the IMD (IMDs commonly have a fixed location and can be easily detected by the physician).

Figure 4A:
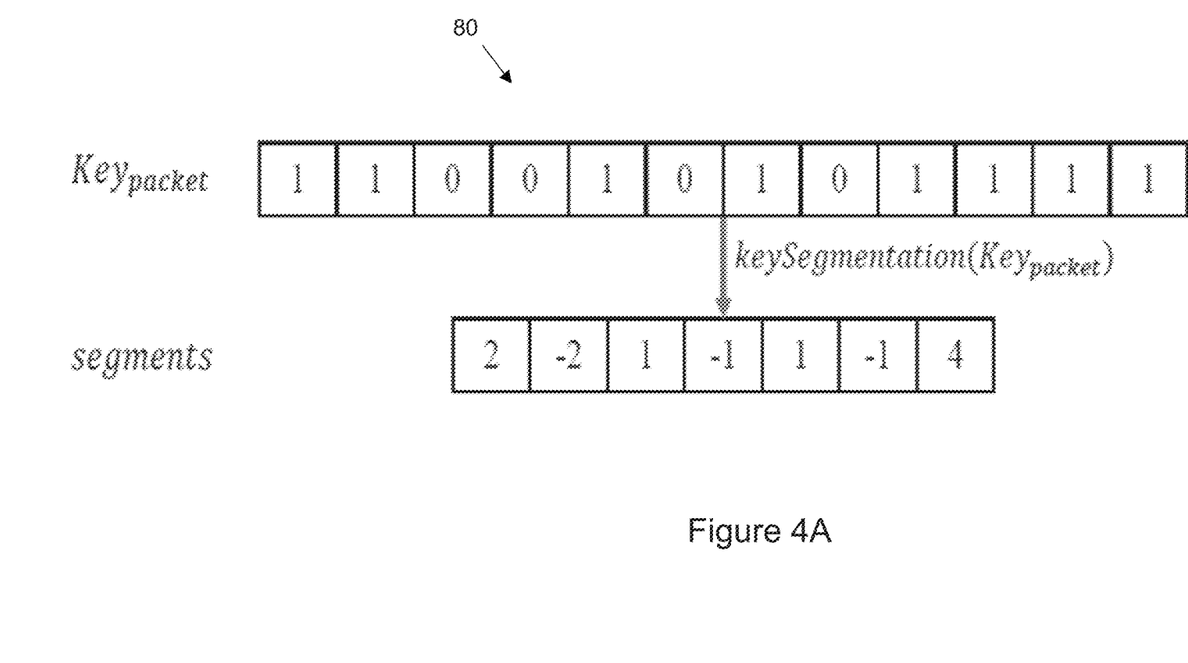
FIG. 4A is block diagram showing keySegmentation outputs segments[ ], given $Key_{packet}$.

Step 3:

The external device uses on-off keying (OOK) modulation to transmit $Key_{packet}$. It should be understood that a variety of modulation schemes may be used without departing from the scope of this disclosure. Examples include but are not limited to on-off keying (OOK), frequency-shift keying (FSK), amplitude-shift keying (ASK), amplitude and phase-shift keying (APSK), continuous phase modulation (CPM), and pulse-position modulation (PPM). The flashlight is turned on (off) for a fixed period of time ($T_{step}$) to transmit bit "1" ("0"). The LED (flashlight) Control procedure disclosed below shows a simplified pseudo-code for this step. It first computes $$T_{step} = \frac{1000}{R} \text{ms},$$

where R is the transmission rate given by the user. Then, it calls the keySegmentation procedure, which divides Key$_{packet}$ into smaller segments such that each segment only includes all "1"s or all "0"s. The keySegmentation procedure outputs an array of integer numbers (segments[ ]) so that: (i) the absolute value of each element in the array represents the length (the number of bits) of each of the above-mentioned segments, and (ii) the sign of the element shows whether bits of the segment are all "1"s or all "0"s, i.e., if all bits in the ith segment are "1", segments[i]>0, otherwise, segments[i]<0. FIG. 4A is block diagram 80 showing keySegmentation outputs segments[ ], given Key$_{packet}$. Finally, the LED (flashlight) Control procedure turns on/off the flashlight with respect to the absolute values of the elements of segments[ ] and T$_{step}$, i.e., Abs(segment) *T$_{step}$ determines how long the flashlight must be kept on/off.

Step 4:

The IMD demodulates the received visible light and recovers Key$_{packet}$. Then, it extracts K from Key$_{packet}$ by removing Pre and Post. Thereafter, it encrypts a fixed pre-defined confirmation message M$_{confirm}$ using K and transmits this message C=ENC(M$_{confirm}$, K) to the smartphone.

Step 5:

The smartphone checks if it can successfully decrypt the received message C using K, i.e., if DEC(C, K)=M$_{confirm}$. If the message can be successfully decrypted, the smartphone knows that the IMD received the key K correctly, and then subsequent RF data transmissions are encrypted using key K.

```
LED (flashlight) Control procedure
Given: The key packet (Key_packet) and transmission rate (R)
    1. T_step ← 1000/R
    2. segments[ ] ← keySegmentation(Key_packet)
    3. For each segment in segments[ ]
        4. If(segment>0)
            5. turnTheLightOn(Abs(segment)*T_step)
        6. else
            7. turnTheLightOff(Abs(segment)*T_step)
        8. end
    9. end
```

In addition to key exchange, the above-mentioned protocol (the first three steps) can be used to transmit data/commands from the smartphone to the IMD without using the RF module. For example, a predefined stream of bits can be reserved for the shutdown command, i.e., a command that entirely disables the device, and sent using this protocol when needed. Note that the IMD cannot provide any feedback via OpSecure since the channel is unidirectional. However, modern IMDs commonly have an embedded beeping component that warn the patient in different scenarios, e.g., when the RF module is activated or when the device's battery level is low. Such a component can also be used to provide feedback when the IMD receives a pre-defined message over OpSecure, e.g., the beeping component can generate three beeps when the IMD receives the shutdown command via OpSecure.

Prototype Implementation

Figure 4B:
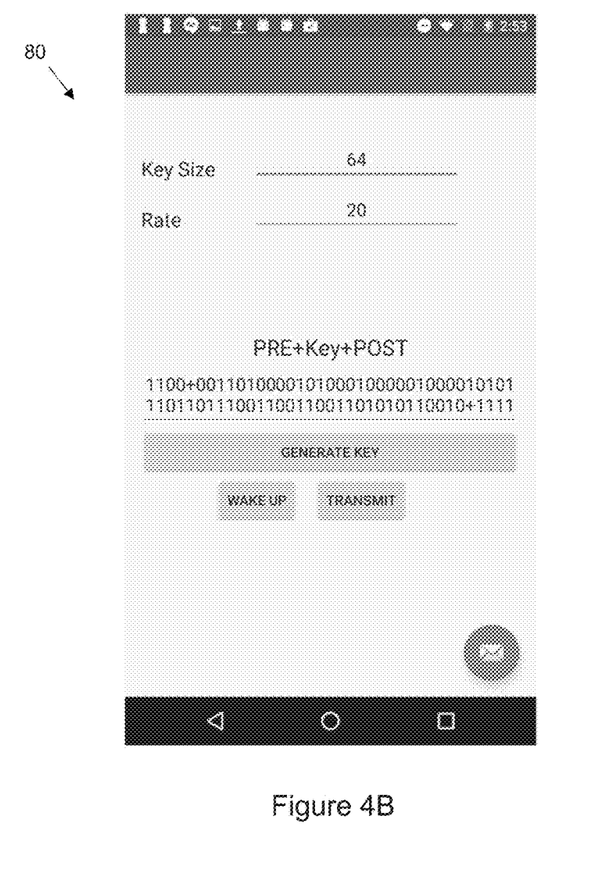
FIG. 4B is a screen shot of and Android application running on the external device configured to generate and transmit a random key to the IMD using the smartphone flashlight.
Figure 5:
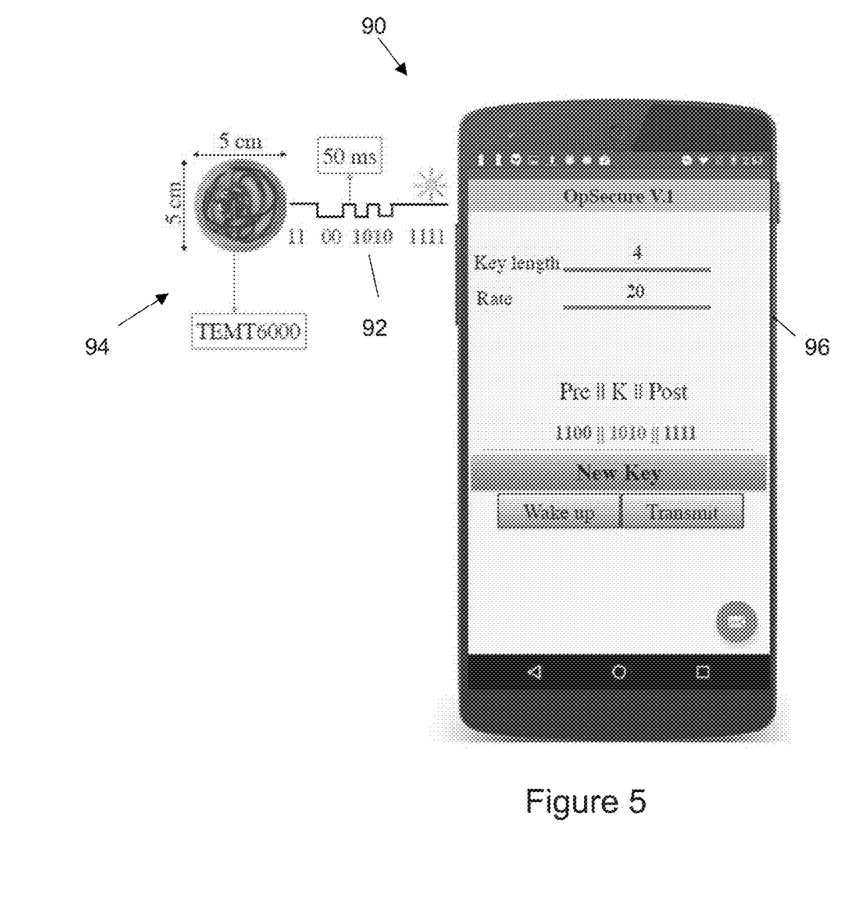
FIG. 5 is a block diagram of a prototype implementation.

FIG. 5 is a block diagram of a prototype implementation 90. As mentioned earlier, a unidirectional optical communication channel 92 is established between the IMD 94 and the external device 96. The prototype system included a wireless-enabled IMD prototype based on digital processor (ATmega168V, a low-power microprocessor from Atmel), a light sensor (TEMT6000, an ambient light sensor from Vishay Semiconductors), an RF communication module (RFD77101, a Bluetooth Low Energy module from Simblee). The prototype system does not offer any health monitoring/therapeutic operations. Indeed, it only implements the two proposed functions disclosed above, a unidirection optical channel and RF key exchange. The processor (TEMT6000) enables RF key exchange only after detecting that visible light generated by the user's smartphone is above a threshold, and the RF module (RFD77101) provides the bidirectional RF communication that can be secured using a symmetric encryption mechanism for which the key can be exchanged over the unidirection optical channel. An Android application was also developed to either wake the IMD up or generate and transmit a random key to the IMD using the smartphone flashlight. The application allows the user to set the key length (N) and transmission rate (R) as shown in FIG. 4B.

FIG. 5 illustrates the prototype system and Android application. It also demonstrates how the application turns the flashlight on/off to transmit the key. For the key exchange example shown in FIG. 5, the key length and transmission rate are set to 4b (in practice, the N used would be much higher) and 20b/s, respectively. Thus, the smartphone needs $$T_{step} = \frac{1000}{20} \text{ms} = 50 \text{ ms}$$

for transmitting a single bit. In this implementation, the application uses two 4-bit sequences ("1100" and "1111") to mark the beginning and end of the key.

It is believed that the smartphone's specifications, in particular the maximum light intensity generated by its flashlight and maximum blinking frequency (i.e., how fast the flashlight can be turned on and off), may affect the experimental results. Thus, the protocols were tested using three different smartphones: The Google Nexus 5s and Nexus 6, and the Motorola MotoX.

The Bacon-Beef Body Model

Figure 6:
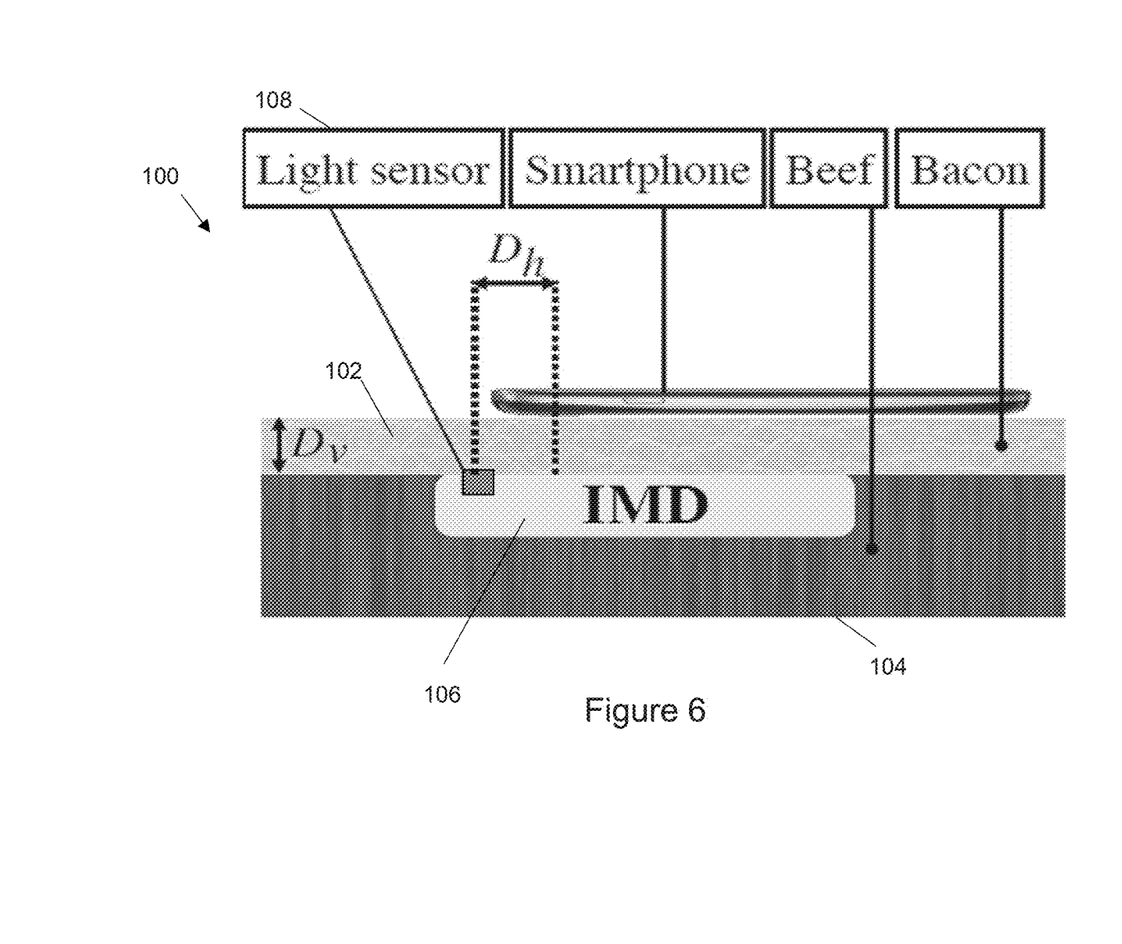
FIG. 6 is a block diagram of an experimental setup using a bacon-beef body model.

FIG. 6 is a block diagram 100 of an experimental setup using a bacon-beef body model. The bacon-beef model for the human body has been previously used in several research studies. Although this model may not fully represent all the characteristics of the human body, it has been accepted as a valid testing methodology by researchers working on IMDs due to the difficulties associated with more realistic experiments, e.g., laws that permit and control the use of animals for scientific experimentation. The bacon-beef body model includes of a thin layer of bacon 102 on a thick layer of 85% lean ground beef 104. In these experiments, the IMD prototype 106 is placed between the thin layer of bacon 102 and the thick layer of ground beef 104, which reflects the typical placement of ICDs in animals or humans. The smartphone is placed on top of the bacon layer 102 (simulating layers of skin and other tissue) above a transparent plastic sealing layer (not shown).

Transmission Range

We evaluated the prototype using the bacon-beef model for the human body. We varied both the vertical distance and horizontal distance between the IMD and the smartphone (shown as D$_v$ and D$_h$ in FIG. 6, respectively) to evaluate the vertical and horizontal transmission range (maximum D$_v$ and $D_h$ at which the visible light can still reach the IMD). We found that both maximum $D_v$ and $D_h$ are independent of the key length and transmission rate. They mainly depend on the maximum light intensity that the flashlight has to offer. For the three smartphones we used in our experiments (Nexus 5s, Nexus 6, and MotoX), the maximum light intensity generated by their flashlights is almost the same. Indeed, for all three smartphones, the maximum vertical (horizontal) transmission range was about 2 cm (1.5 cm). Thus, if the physician places the smartphone on the patient's body and keeps the smartphone within 1.5 cm of the IMD's light sensor ($D_h$<1.5 cm), the visible light can easily reach a depth of 1 cm (the typical $D_v$ for IMDs, such as ICDs). The IMD location is fixed and easily recognizable by inspecting the patient's skin under which the IMD is implanted. Therefore, ensuring $D_h$<1.5 cm would be straightforward for a physician.

Wakeup/Exchange Time

Next, we evaluated the wakeup time (the time that the wakeup protocol takes to detect the presence of the external device and turn on the RF module) and the exchange time (how long the key exchange protocol takes to exchange the encryption key).

Wakeup Time:

As mentioned above, the wakeup protocol periodically places the light sensor in the full operating mode, in which the sensor samples the light intensity, to check if the smartphone flashlight is present. The wakeup time depends on two parameters: (i) how long the light sensor is in the full operating mode ($T_{operation}$), and (ii) how long the light sensor remains in the standby mode ($T_{standby}$) in which the sensor is disabled. $T_{operation}$ and $T_{standby}$ should be set with regard to the maximum tolerable wakeup time and energy consumption of the wakeup protocol. For example, if we set $T_{standby}$=0.8 s and $T_{operation}$=0.2 s, the IMD turns on the light sensor for 0.2 s and then disables it for 1.8 s. In this case, the worst-case wake up time will be $T_{standby}+T_{operation}$=2 s. As described later, the worst-case wakeup time can be traded off against energy consumption by varying either $T_{standby}$ or $T_{operation}$.

Exchange Time:

The exchange time can be readily calculated as $T_{EX}$=N/R, where N and R are the key length and transmission rate, respectively. N depends on the encryption mechanism and is commonly 64b or 128b. The transmission rate generally depends on two parameters: (i) the blinking frequency, and (ii) how fast the light sensor can sample the visible light. In our experiments, the maximum blinking frequency offered by the smartphones was within a 20-30 Hz range, and the light sensor was able to sample visible light with a sampling rate of a few hundred Hz (a sampling rate of 60 Hz is sufficient to recover the key when the blinking frequency is 30 Hz). Therefore, the maximum blinking frequency of the smartphone flashlight limited the transmission rate. In fact, the maximum transmission rate was within the range of 20b/s (for MotoX) to 30b/s (for Nexus 6). As a result, the minimum time needed for exchanging a packet, that includes a key of length 64b (128b) and both Pre and Post, was within the range of 2.4 s to 3.6 s (4.5 s to 6.8 s).

Note that different smartphones may offer different maximum transmission rates. However, the IMD does not need to know the transmission rate R beforehand since R can be computed based on the binary sequence Pre, which is known to the IMD. In our prototype implementation, where the first two bits of Pre are always "11" (as mentioned above, Pre="1100"), R can be computed as follows:

$$R = \frac{1000}{T_{step}} \text{ms, where } \frac{1000}{T_{step}} \text{ms}$$

is half of the duration of the time frame in which the IMD observes the Pre sequence.

Size and Energy Overheads

Next, we examine the size and energy overheads that the proposed protocols add to the IMD. Light sensors commonly include a phototransistor in series with a small resistor that converts received light to a voltage. Light sensors typically also have an analog-to-digital converter (ADC) that converts this voltage to a digital number. Thus, a light sensor includes simple circuitry that can be implemented in a very small area. To save more area on the chip, manufacturers may also use an ADC already incorporated into the IMD and just add a phototransistor/resistor. In both cases, the size overhead is negligible.

The energy overhead is the additional energy consumed by the light sensor, which is added to the IMD to enable transmission over OpSecure. The energy consumption of a light sensor (even one with a built-in ADC) is typically very small, and thus results in negligible energy overhead on the IMD. We investigate the energy overheads for each protocol using a realistic example next.

Consider a typical ICD with a 1.5-Ah battery and 90-month lifetime (it consumes about 23.14 μA current on an average). We can either use a light sensor with a built-in ADC such as MAX44007 or a light sensor without an ADC such as TEMT6000 (used in our prototype). Next, we discuss the energy overheads of wakeup and key exchange protocols for the ICD in both cases.

Wakeup Protocol:

We configure the IMD so that the light sensor is in the full operating mode for $T_{operation}$=0.2 s after being in the standby mode for $T_{standby}$=1.8 s. Thus, the light sensor only spends 10% of the time in the full operating mode. MAX44007 drains 0.65 μA (100 pA) from the battery in the full operating (standby) mode, thus draining 65.09 nA on an average. In this case, the energy overhead of the wakeup protocol is less than 0.3% of the total energy consumption. If we use TEMT6000, the phototransistor in series with the resistor and the built-in ADC, when operating in the full operating mode, drain a few nA and tens of nA from the battery, respectively. Therefore, their energy overheads are negligible in comparison to the total energy consumption of the ICD. Reducing $$\frac{T_{operation}}{T_{operation} + T_{standby}}$$

makes the energy overhead even smaller.

Key Exchange Protocol:

After waking up the RF module, the physician can use the smartphone to initiate the key exchange procedure in which the IMD configures the light sensor to sense light in the full operating mode for a few seconds. However, key exchange is a very rare event for two reasons. First, a key that is exchanged once can typically be used for a long period of time unless the user suspects that the key is compromised. Second, the communication between the IMD and the external device is very sporadic (e.g., the number of transmissions varies from a few times per day to a few times per year). Thus, even if the external device transmits a new key for each communication session, the timeframe in which the light sensor operates in the full operating mode to exchange the key is negligible in comparison to the device lifetime. Consequently, the key exchange protocol adds almost-zero energy overhead to the IMD.

Threat Model

An attacker can be any unauthorized person who has a short-term proximity to the subject. He might attempt to (i) target the wakeup protocol to launch a battery draining attack, (ii) inject his arbitrary encryption key into OpSecure, or (iii) eavesdrop on OpSecure to extract the encryption key. The first two attacks against OpSecure are active attacks in which the attacker interferes with the wakeup or key exchange protocol and sends unauthorized messages to the IMD, whereas the third attack is a passive attack, in which the attacker only monitors the ongoing communications.

If the attacker is able to extract the encryption key (either passively or actively), he can steal sensitive medical information from the patient and/or send unauthorized commands to the IMD, causing the device to malfunction. Potential attackers might be criminal groups that want to sell sensitive medical data to the highest bidder or launch life-threatening attacks against a person of interest, political operatives who intend to exploit medical issues of the subject for their political advantage, or employers who discriminate against a group of ill employees.

Resiliency Against Security Attacks

Next, we consider both active and passive attacks.

Active attacks: We discuss the feasibility of two active attacks against OpSecure: remote activation of the RF module and key injection.

As mentioned earlier, the horizontal transmission range is about 1.5 cm and the physician should keep the smartphone within this range to wake up the IMD or transfer the key. Due to this proximity requirement, the attacker cannot place an unauthorized smartphone on the patient's body within the horizontal transmission range without raising suspicion.

Moreover, as mentioned above, the presence of an external powerful light source, which is not attached to the body, does not affect the intensity of the light received by the in-body light sensor. Thus, it cannot be used to launch an active attack against the IMD. To further examine the feasibility of active attacks using external light sources, we replaced the external light source with a laser generating coherent light (with the power of 25 mW). In this scenario, the laser was located 1 m away from the IMD and pointed toward the light sensor of the IMD. We observed that the coherent light is not able to sufficiently penetrate the bacon layer used in our experimental setup (FIG. 6) to reach the IMD and, therefore, it cannot be used by the attacker to activate the wakeup protocol or inject the encryption key.

The above-mentioned experiments demonstrate that the attacker can neither attach a device to the patient's body without raising suspicions nor remotely (i.e., without physical contact) attack the device.

Passive attack: We examined the possibility of eavesdropping using two different experimental scenarios, as described next.

1. Near-IMD attack: We first placed the smartphone on the chest of a human subject and placed a light sensor close to the smartphone to measure the light intensity on the body surface at varying distances from the smartphone flashlight. As expected, the visible light attenuated very fast and the light sensor was not able to detect the light from the flashlight as the distance between them became greater than 2 cm. Thus, an eavesdropping device to pick up the light and extract the key would need to be placed on the body surface within 2 cm of the IMD, which is not likely to be feasible since the patient can easily detect such a device.

2. Remote attack: We next investigated the feasibility of launching remote eavesdropping (without an on-body sensor). We noticed that the smartphone flashlight creates a red circular area on the user's chest when it is on. We investigated if an attacker may be able to use a camera to capture a video from the user's chest and process the video to extract the key. In order to examine the feasibility of such an attack, we asked a subject to hold the smartphone over his chest. Then, we placed a 12-megapixel camera at a distance of 1 m (a reasonable distance for remote eavesdropping) from the user's chest, and captured two sets of videos in a dark room: four videos when the smartphone flashlight was on and four when the flashlight was off. The videos were captured in the dark room to simulate the worst-case scenario since the effect of ambient light sources is minimized and, as a result, the red spot created by the flashlight becomes more visible. We extracted 1000 frames from each video. For each video in the first set, we compared all of its frames to the ones of all videos in the second set using the concept of RGB Euclidean distance. This is a metric that represents the color difference between two frames. For each video in the first set, the RGB Euclidean distances between its frames and the frames of other videos in the first set were similar to distances between its frames and the frames of videos in the second set, i.e., the videos in the first set were not distinguishable from the videos in the second set. This indicates that the attacker cannot detect the red spot created by the smartphone flashlight when the smartphone is placed on the user's chest. Thus, in this scenario, the attacker cannot distinguish bit "1" from "0" when the key exchange protocol is sending the key.

Further disclosure is contained in U.S. provisional application No. 62/409,083 filed Oct. 17, 2016 and its Appendix, which are incorporated herein in their entirety. Any references cited in the Appendix of U.S. provisional application No. 62/409,083 filed Oct. 17, 2016 are also are incorporated herein in their entirety. It should be understood that many variations are possible based on the disclosure herein. Although features and elements are described above in particular combinations, each feature or element can be used alone without the other features and elements or in various combinations with or without other features and elements. The digital processing techniques disclosed herein may be partially implemented in a computer program, software, or firmware incorporated in a computer-readable (non-transitory) storage medium for execution by a general-purpose computer or a processor. Examples of computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

Suitable processors include, by way of example, a general-purpose processor, a special purpose processor, a conventional processor, a digital signal processor (DSP), a plurality of microprocessors, one or more microprocessors in association with a DSP core, a controller, a microcontroller, Application-Specific Integrated Circuits (ASICs), Field-Programmable Gate Arrays (FPGAs) circuits, any other type of integrated circuit (IC), and/or a state machine.

What is claimed is:

1. An implantable medical device (IMD) configured to communicate with an external device (ED), the ED being configured to support two-way RF communications and having a light source, the IMD comprising:

a processor coupled to an optical detector, the processor being configured to verify that light is being received from the ED light source and that the ED is a trusted device by determining that an intensity of the light being received from the ED light source is above a predetermined threshold, establishing a unidirectional optical channel from the ED to the IMD; and an RF transceiver coupled to the processor, the processor being configured permit two-way RF communications with the ED only under a condition that the ED is verified as a trusted device, wherein the processor is further configured to detect a multi-bit message from the ED via the unidirectional optical channel, wherein the multi-bit message includes a key for use in encrypting and decrypting RF communication with the ED, wherein the multi-bit message also includes a pre sequence received prior to the key and a post sequence received after the key, and wherein the processor is further configured to determine the transmission rate of the ED light source based on the pre sequence.

2. The IMD of claim 1 wherein the processor is configured to wake up periodically or aperiodically to check for the presence of light from the ED light source.

3. The IMD of claim 1 wherein the multi-bit message includes data or a command for the IMD.

4. The IMD of claim 1 wherein the ED is configured to transmit the multi-bit message using a modulation scheme.

5. The IMD of claim 4 wherein the modulation scheme includes at least one of on-off keying (OOK), frequency-shift keying (FSK), amplitude-shift keying (ASK), amplitude and phase-shift keying (APSK), continuous phase modulation (CPM) and pulse-position modulation (PPM).

6. The IMD of claim 1 wherein following verification that the ED is a trusted device the processor is configured to support encrypted communication via the RF transceiver using the key obtained via the unidirectional optical channel.

7. The IMD of claim 6 wherein the processor is configured to generate a confirmation message encrypted using the key, the processor being configured to transmit the confirmation message to the ED via the RF transceiver.

8. The IMD of claim 7 wherein the ED is configured determine whether the confirmation message can be successfully decoded using the key and only under this condition the ED is configured to support subsequent bi-directional RF communications with the IMD encrypted using the key.

9. A method of communicating using an implantable medical device (IMD) configured to communicate with an external device (ED), the ED being configured to support two-way RF communications and having a light source, the method comprising:

providing a processor coupled to an optical detector, the processor being configured to verify that light is being received from the ED light source and that the ED is a trusted device by determining that an intensity of the light being received from the ED light source is above a predetermined threshold, establishing a unidirectional optical channel from the ED to the IMD; and providing an RF transceiver coupled to the processor, the processor being configured permit two-way RF communications with the ED only under a condition that the ED is verified as a trusted device, wherein the processor is further configured to detect a multi-bit message from the ED via the unidirectional optical channel, wherein the multi-bit message includes a key for use in encrypting and decrypting RF communication with the ED, wherein the multi-bit message also includes a pre sequence received prior to the key and a post sequence received after the key, and wherein the processor is further configured to determine the transmission rate of the ED light source based on the pre sequence.

10. The method of claim 9 wherein the processor is configured to wake up periodically or aperiodically to check for the presence of light from the ED light source.

11. The method of claim 9 wherein the multi-bit message includes data or a command for the IMD.

12. The method of claim 9 wherein the ED is configured to transmit the multi-bit message using a modulation scheme.

13. The method of claim 12 wherein the modulation scheme includes at least one of on-off keying (OOK), frequency-shift keying (FSK), amplitude-shift keying (ASK), amplitude and phase-shift keying (APSK), continuous phase modulation (CPM) and pulse-position modulation (PPM).

14. The method of claim 9 wherein following verification that the ED is a trusted device the processor is configured to support encrypted communication via the RF transceiver using the key obtained via the unidirectional optical channel.

15. The method of claim 14 wherein the processor is configured to generate a confirmation message encrypted using the key, the processor being configured to transmit the confirmation message to the ED via the RF transceiver.

16. The method of claim 15 wherein the ED is configured determine whether the confirmation message can be successfully decoded using the key and only under this condition the ED is configured to support subsequent bi-directional RF communications with the IMD encrypted using the key.

17. The method of claim 9, wherein the ED light source is a light on a smartphone held no more than 1.5 cm from the IMD.

18. The method of claim 9, wherein the transmission rate is half the duration of a time frame in which the IMD detects the pre sequence.

* * * * *